US011663735B2

(12) United States Patent
Balakrishnan et al.

(10) Patent No.: US 11,663,735 B2
(45) Date of Patent: May 30, 2023

(54) OPTICAL MARKERS FOR CALIBRATION/ALIGNMENT OF MEDICAL DIAGNOSTIC DEVICES

(71) Applicant: CANON MEDICAL SYSTEMS CORPORATION, Otawara (JP)

(72) Inventors: Karthikayan Balakrishnan, Vernon Hills, IL (US); Kent C. Burr, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 311 days.

(21) Appl. No.: 17/015,670

(22) Filed: Sep. 9, 2020

(65) Prior Publication Data

US 2022/0076439 A1   Mar. 10, 2022

(51) Int. Cl.
*G06K 9/00* (2022.01)
*G06F 1/00* (2006.01)
*G06T 7/70* (2017.01)
*A61B 6/04* (2006.01)
*G06T 7/00* (2017.01)
*A61B 6/03* (2006.01)
*A61B 90/00* (2016.01)

(52) U.S. Cl.
CPC .............. *G06T 7/70* (2017.01); *A61B 6/0407* (2013.01); *A61B 6/0492* (2013.01); *G06T 7/0012* (2013.01); *A61B 6/032* (2013.01); *A61B 6/037* (2013.01); *A61B 2090/3937* (2016.02); *A61B 2090/3979* (2016.02); *G06T 2207/10048* (2013.01); *G06T 2207/30004* (2013.01); *G06T 2207/30204* (2013.01)

(58) Field of Classification Search
CPC ............ G06K 9/00; G01R 33/283; G06F 1/00

USPC ........ 382/100, 103, 106–107, 128–132, 154, 382/168, 173, 181, 199, 216, 220, 232, 382/254, 276, 285–291, 305, 321; 324/318; 600/407; 901/47
See application file for complete search history.

(56) References Cited

U.S. PATENT DOCUMENTS

| 2007/0053486 | A1 | 3/2007 | Zelnik et al. |
| 2010/0156421 | A1* | 6/2010 | Sukkau ............... G01R 33/3415 324/318 |
| 2014/0049629 | A1 | 2/2014 | Siewerdsen et al. |

(Continued)

FOREIGN PATENT DOCUMENTS

WO     02/080773 A1    10/2002

OTHER PUBLICATIONS

Wei, et al. ; PET/CT alignment calibration with a non-radioactive phantom and the intrinsic 176 Lu Radiation of PET detector ; Nuclear Instruments and Methods in Physics Research Section A: Accelerators, Spectrometers, Detectors and Associated Equipment, vol. 835 ; pp. 163-168 ; Nov. 1, 2016 ; Abstract Only ; 1 Page.

*Primary Examiner* — Seyed H Azarian
(74) *Attorney, Agent, or Firm* — Oblon, McClelland, Maier & Neustadt, L.L.P.

(57) ABSTRACT

Optical sensors and optical markers are placed on components in a medical system to provide calibration and alignment, such as on a patient transportation mechanism and spatially separated medical diagnostic devices. Image processing circuitry uses the data captured by these optical devices to coordinate their movements and/or position. This enables scans that were captured in multiple medical diagnostic devices to be accurately aligned.

22 Claims, 17 Drawing Sheets

(56) References Cited

U.S. PATENT DOCUMENTS

| | | | | |
|---|---|---|---|---|
| 2015/0297177 A1* | 10/2015 | Boctor | ............... | A61B 34/30 |
| | | | | 901/47 |
| 2016/0073962 A1* | 3/2016 | Yu | .................. | G01R 33/283 |
| | | | | 600/407 |
| 2017/0079722 A1* | 3/2017 | O'Grady | ............. | A61B 90/90 |
| 2017/0319143 A1* | 11/2017 | Yu | ..................... | A61B 5/682 |
| 2020/0016758 A1* | 1/2020 | Keller | ................ | B25J 9/1692 |

\* cited by examiner

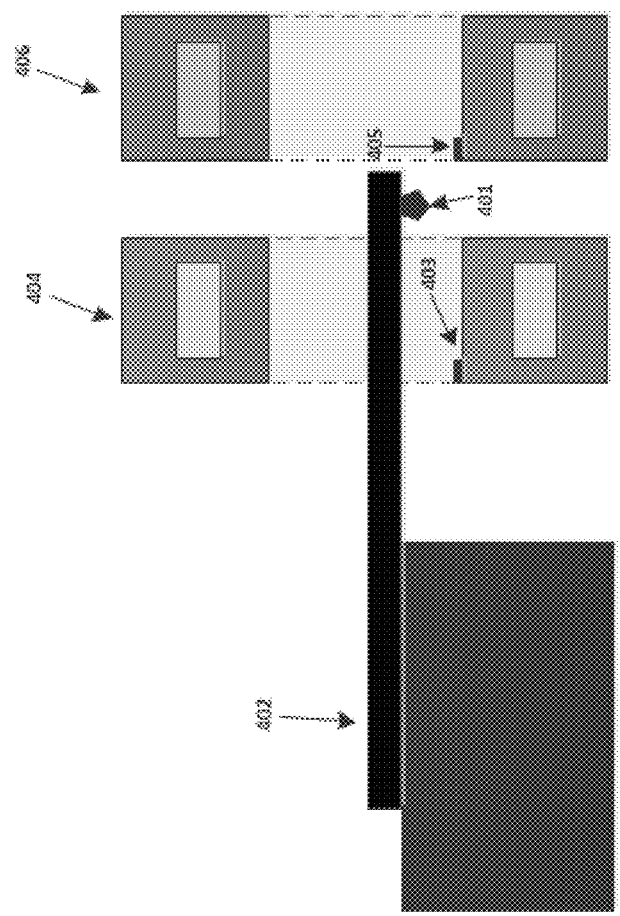

OPTICAL MARKERS FOR CALIBRATION/ALIGNMENT OF MEDICAL DIAGNOSTIC DEVICES

FIELD OF THE INVENTION

The method and system described herein are directed to providing alignment of components in a medical system including multiple medical diagnostic devices, and, in one embodiment, to utilizing optical markers and optical sensors to control movement of and/or detect a location of a patient transportation mechanism such that medical information obtained by the multiple medical diagnostic devices can be calibrated/aligned.

BACKGROUND

Known combined PET/CT scanner systems produce respective medical images that are taken at spatially separate locations because the PET and CT images are generated by spatially separated medical diagnostic devices (e.g., scanners), even when the combined system utilizes a single patient transportation mechanism that moves between the scanners. Using such a combined system, it is possible to use alignment/calibration information to transform the respective images to a common reference frame in order to "fuse" the respective images. This fused image (e.g., a CT/PET image) may aid medical professionals in understanding the information obtained by the scanners more effectively that using the respective images individually.

Knowing the relative and/or absolute location of components (such as the patient transportation mechanism and the medical imaging devices) in an imaging system enables more effectively fused images to be created. One method for doing so requires a calibration between the various components. A number of issues arise when performing these calibrations and attempting to keep components calibrated. For example, often valuable scanner operating time is used for re-calibration when even minor maintenance operations are performed. One such realignment often occurs in case an offset is created or changed during the process of separating gantries and bringing the gantries back together. In such a realignment, a calibration can be stored for future use (i.e., pre-stored) until the gantries are separated again.

Dynamic calibration, rather than a pre-stored calibration, can also be required such as when a heavy patient is held by a cantilevered patient transportation mechanism during imaging. As the bed moves between the gantries, the bed deflection introduces an offset that may not be sufficiently captured by a single pre-stored calibration provided by using a single phantom (which did not produce similar bed deflection during calibration).

Furthermore, some known calibrations cannot be performed in darkness even though darkness is necessary to some functional imaging. Implementations of this invention using visible light might interfere with some functional imaging (such as measuring the response in PET or MM to visual stimulation). For these cases, the invention could be implemented using cameras (optical sensors) which image invisible radiation, such as infrared.

SUMMARY

To address at least one problem identified with known techniques, the present disclosure describes using image processing to address alignment/calibration issues between various components of a medical diagnostic system (e.g., PET/CT imaging system) that can be accessed via a common patient transportation mechanism (e.g., patient bed). This disclosure will use a PET/CT system to illustrate exemplary embodiments, but other environments, such as a PET/MRI scanner system, can benefit from the teachings herein.

An apparatus is described for calibrating movement of and/or a position of a patient transportation mechanism shared between multiple medical diagnostic devices. In one exemplary embodiment, the apparatus includes (1) a first set of coordinating optical devices including at least one optical marker; (2) a second set of coordinating optical devices including at least one optical sensor for detecting the at least one optical marker, and (3) image processing circuitry configured to determine a position of the patient transportation mechanism from a position of the at least one optical marker relative to the at least one optical sensor. The location of and the number of components of the first and second sets of coordinating optical devices vary in the exemplary embodiments described herein. In general, at least one component of one of the first and second sets of coordinating optical devices is configured to be affixed to the patient transportation mechanism, and at least one component of a remaining one of the first and second sets of coordinating optical devices is configured to be affixed to at least one of first and second medical diagnostic devices.

In one embodiment, at least one optical sensor is mounted on the gantries, at least one optical marker is affixed to the patient transportation mechanism, and image processing circuitry determines the patient transportation mechanism's position and/or orientation relative to at least one of the at least one optical marker and the at least one optical sensor.

In another embodiment, one or more cameras are mounted on the patient transportation mechanism, and one or more tags are mounted on the gantries. Image processing circuitry determines the patient transportation mechanism position and orientation relative to the tags.

Additional embodiments could comprise image processing that measures deflection of the patient transportation mechanism, optical markers that are machined into the patient transportation mechanism or gantry during the manufacturing process, multiple camera inputs that can be used for signal averaging (e.g. telephoto lens, wide lens, thermal camera), tags that produce heat/thermal signatures, and more.

This summary section does not specify every embodiment and/or incrementally novel aspect of the present disclosure or claimed invention. Instead, this summary only provides a preliminary discussion of different embodiments and corresponding points of novelty. For additional details and/or possible perspectives of the invention and embodiments, the reader is directed to the Detailed Description section and corresponding figures of the present disclosure as further discussed below.

BRIEF DESCRIPTION OF THE DRAWINGS

FIGS. 4A and 4B illustrates a second configuration of a second exemplary embodiment of a medical device calibration system.

DETAILED DESCRIPTION

Figure 1:
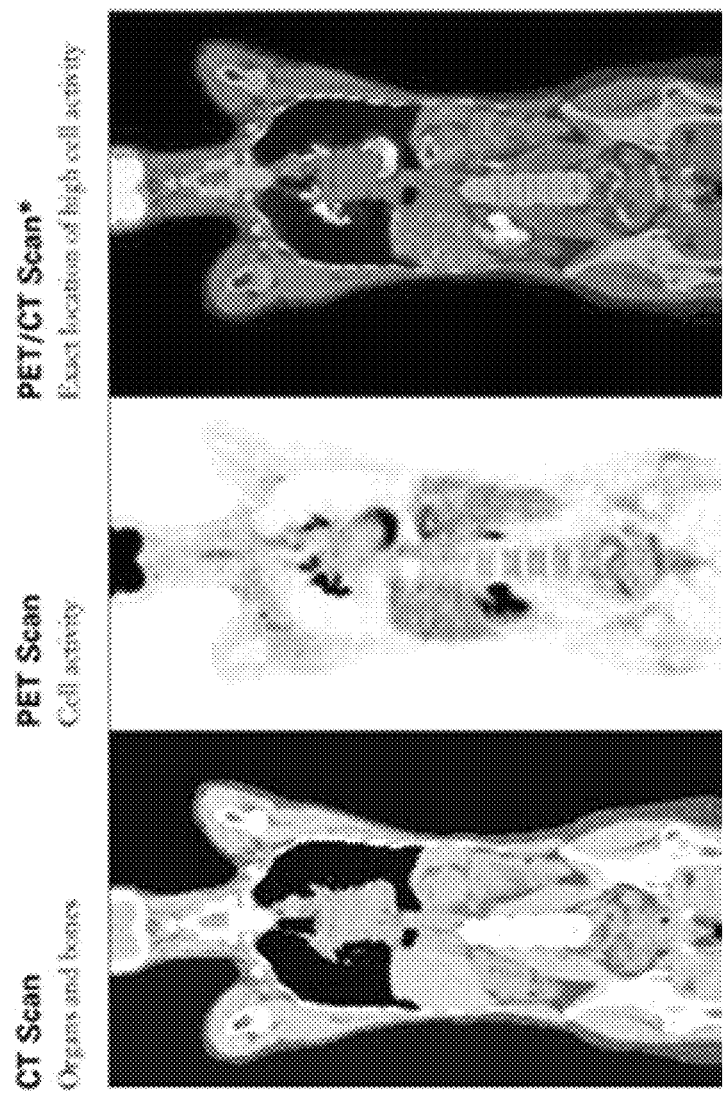
FIG. 1 is a composite image showing a CT scan image, PET scan image, and a corresponding PET/CT scan image.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways. This disclosure will use a PET/CT scan to illustrate the various embodiments, but the same techniques can be applied to other scenarios, such as a PET/MRI scan.

Figure 2A:
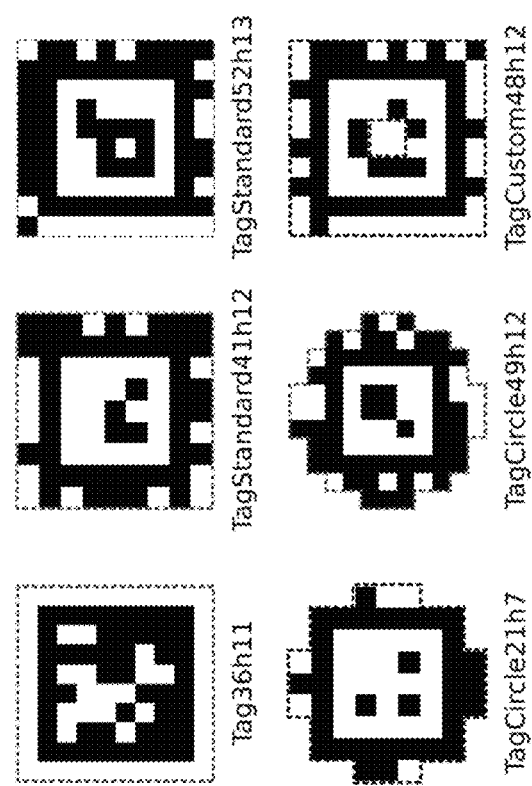
FIGS. 2A and 2B are examples of optical markers.
Figure 2B:
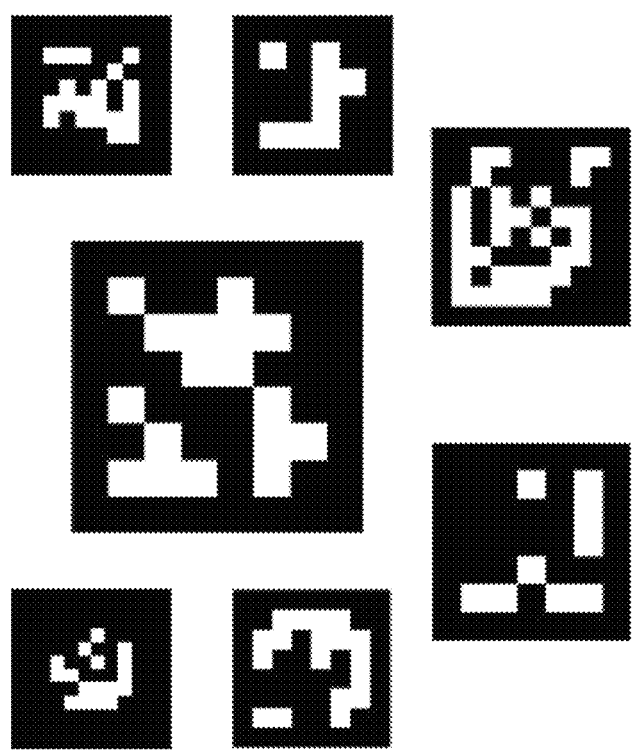

A general PET/CT scan requires multiple gantries which are spatially separated. An alignment calibration that transforms each image to a common reference frame is performed to fuse the PET and CT images. This fused image is more valuable than the sum of its parts, as illustrated in FIG. 1. Coordinating optical devices can be utilized to align the PET and CT image to a common reference frame, where one set of coordinating optical devices comprises at least one optical marker, and a second set of coordinating optical devices comprises at least one optical sensor. One example of an optical marker is a two-dimensional barcode (e.g., a tag) that encodes particular reference information, such as those shown in FIGS. 2A and 2B. These tags can be placed on the medical diagnostic devices (e.g., gantries) or patient transportation mechanism (e.g., a patient bed) and detected by one or more optical sensors (e.g., a camera). In such configurations, image processing circuitry can extract each marker's position, orientation and identity. From a single camera, six degrees of freedom (e.g. origin, x=0, y=0, z=0, and orientation of x, y, and z axis) can be determined with varying degrees of accuracy. Using multiple cameras imaging the same tag from different viewpoints can increase the accuracy. Because determining the camera position from these tags is very cost effective, fast and robust, the alignment calibration can be performed for every scan if desired. This is in effect a dynamic, self-calibrating alignment scan for two separate medical diagnostic devices that are spatially separated and where a common patient transport mechanism is used. The examples of binary square fiducial markers shown in FIG. 2B offer a combination of high contrast features, identity encoding, and unambiguous orientation determination capability which are very useful in unconstrained measurement problems. For the cases described in this disclosure where the general positions of markers can be known and where movements are mostly constrained to known ranges, a wide range of markers can be used, as long as they offer sufficient contrast for imaging by the optical sensors.

Various combination of optical sensors and markers can be used to perform, monitor and maintain the various calibrations as described herein. For example, one calibration determines the offset between the first medical diagnostic device relative to the second medical diagnostic device. During the process of separating gantries and bringing them back together, offset can be introduced, which typically requires recalibration. This calibration to determine the offset between the two medical diagnostic devices can identify offsets and even compensate for it when fusing the scan data. Throughout this disclosure, this calibration will be referred to as the gantry-to-gantry-calibration. Likewise, a second calibration determines the position and orientation of the patient transportation mechanism relative to each respective medical diagnostic device, and will be referred to hereafter as the gantry-to-bed calibration.

In this first exemplary embodiment, one or more cameras serving as the optical sensors are placed on the patient transportation mechanism, and one or more two-dimensional barcodes serving as the optical markers are placed on the gantries. Each gantry can have one or more markers/tags firmly attached to it in different, but known positions. The geometrical design of the scanner is used to decide where to place the markers. The camera(s) attached to the patient transportation mechanism scan these markers throughout the PET/CT imaging process. FIGS. 3A-3E shows some examples of layouts incorporating this embodiment.

Figure 3A:
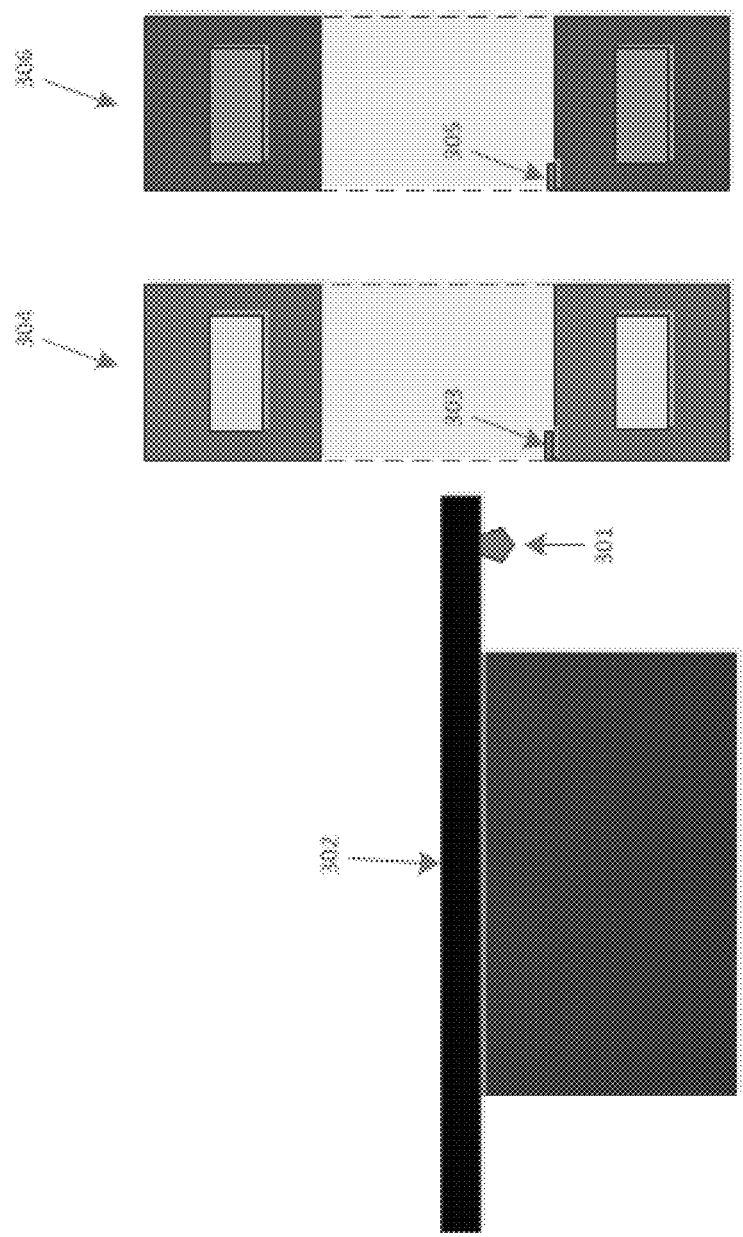
FIGS. 3A-3E illustrate a first configuration of a first exemplary embodiment of a medical device calibration system as a patient bed progresses from outside first and second medical diagnostic devices to inside the first and second medical devices.

In FIG. 3A, no patient imaging is taking place. The setup may look like this prior to scanning or as a default setup. A camera 301 is attached to the patient bed 302, a first marker 303 is placed on the first medical diagnostic device 304, and a second marker 305 is placed on the second medical diagnostic device 306. The patient transportation mechanism 302 has not yet entered into the first medical diagnostic device 304. In this embodiment the first medical diagnostic device 304 is illustrated as the CT gantry and the second medical diagnostic device 306 is illustrated as the PET gantry. Note though that the gantry scanning order does not matter. In other words, the first medical diagnostic device could be the PET gantry, MRI gantry, etc. in other embodiments.

The gantry-to-gantry calibration can be performed any time before the images are fused together, including while in the layout shown in FIG. 3A. As long as the camera 301 has vision to the first marker 303 and second marker 305, the position information can be captured. From there, the processing circuitry can calculate the gantry offset. If the gantry offset is not at default (i.e. the last computed offset), an alert or error message could be triggered. Additionally or alternatively, the patient scans could be taken with this new gantry offset, and the image processing circuitry could account for this new offset when fusing the PET and CT images.

Figure 3B:
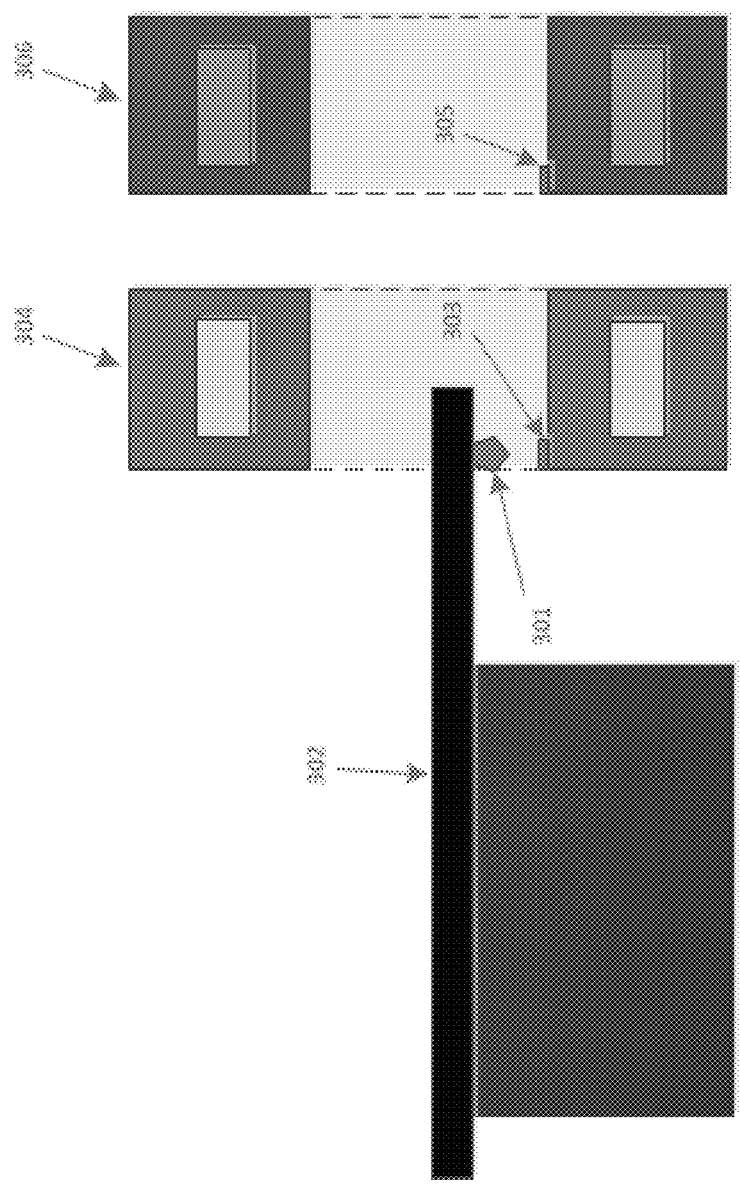

In FIG. 3B, the patient bed 302 has entered into the first medical imaging device 304. The gantry-to-bed calibration of the first gantry 304 can be performed here, where the camera 301 captures the position data of the first marker 303 relative to itself for the processing circuitry to process.

Machine learning software enables the camera 301 to recognize the first marker 303 on the first gantry 304 and the second marker 305 on the second gantry 306, and image processing circuitry uses the data received by the camera and marker combinations to determine the location and orientation of each optical marker. All the captured results (e.g. distance from the marker to the camera, angle from the marker to the camera, rotated orientation of the gantry to the camera, etc.) are processed by the processing circuitry so that they can be fused after all the imaging has occurred.

Figure 3C:
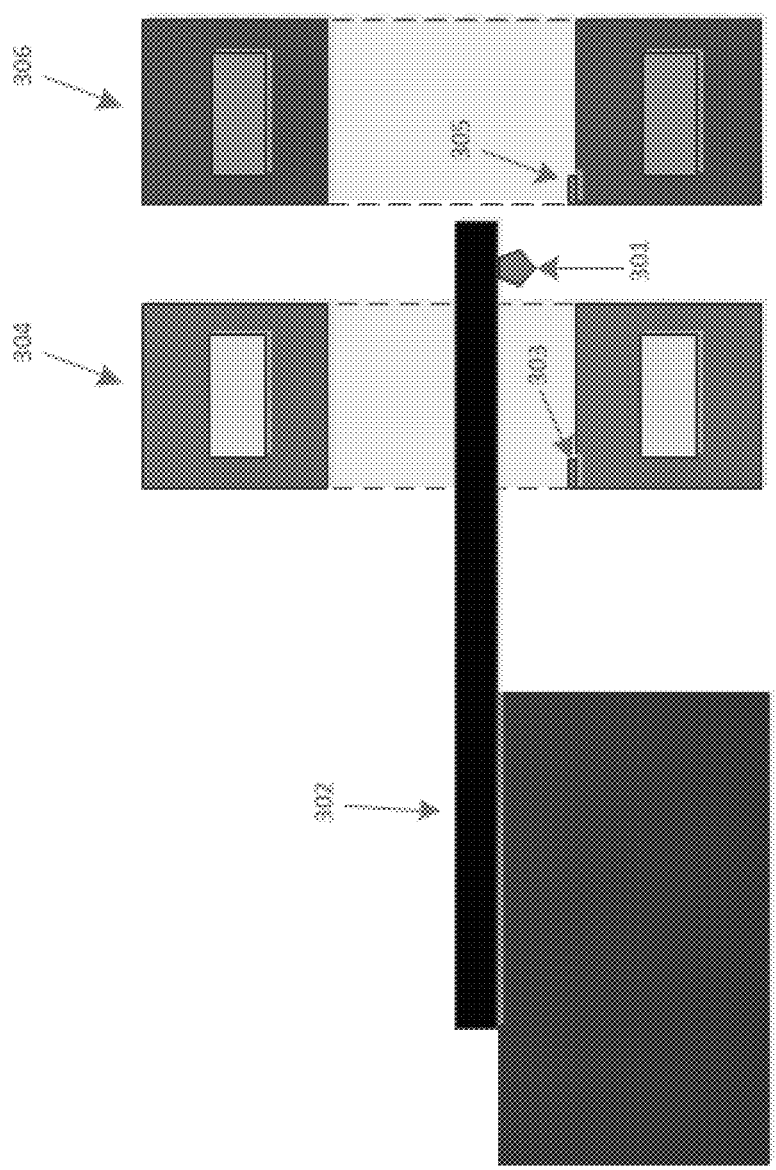

In FIG. 3C, the end of the patient bed 302 is located between the first gantry 304 and second gantry 306. Even though the camera 301 has passed the first gantry 304, if the camera 301 has visibility to the first marker 303 on the first gantry 304, any patient images taken from the first gantry 304 can still be calibrated and fused by the processing circuitry. If all the necessary imaging and position information from the first gantry 304 has already been captured, line-of-sight is desired, but not absolutely required.

Figure 3D:
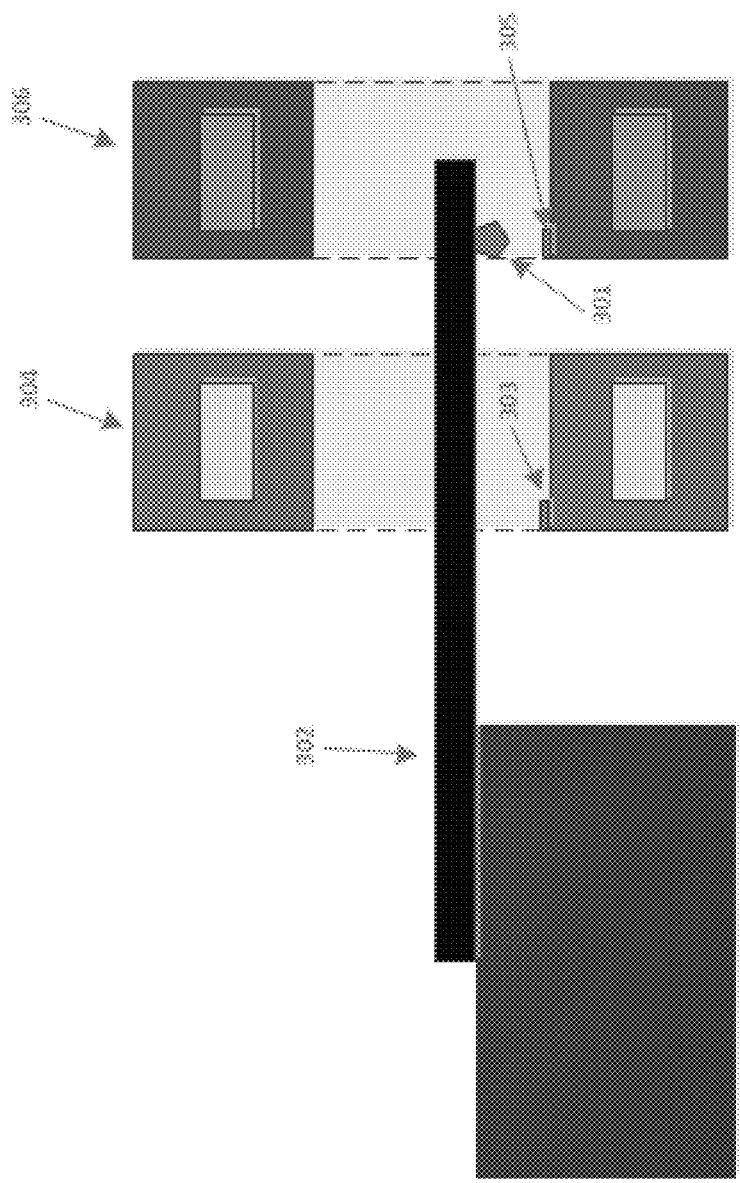

In FIG. 3D, the patient bed 302 has entered into the second medical imaging device 306. The gantry-to-bed calibration for the second gantry 306 could be performed here prior to patient scans taking place, the camera 301 can capture the image of the marker 305 and the processing circuitry can extract the marker's 305 position data.

Figure 3E:
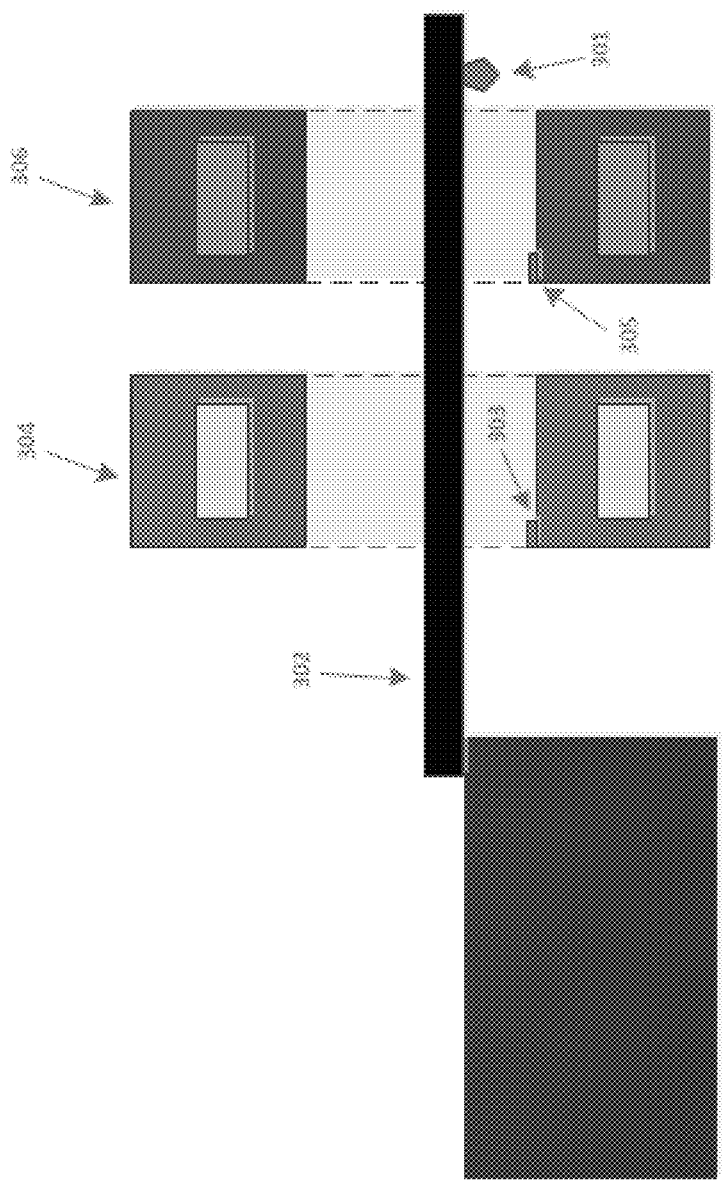

In FIG. 3E, the camera 301 has passed through both gantries. Images of the patient can be taken in this layout. As long as the camera 301 has visibility to the marker 303 on the first gantry 304, as well as visibility to the marker 305 on the second gantry 306, calibration/coordination can be monitored in the respective gantries. Once the patient's scans are complete, both patient scan data and PET/CT alignment data is generated.

Figure 4B:
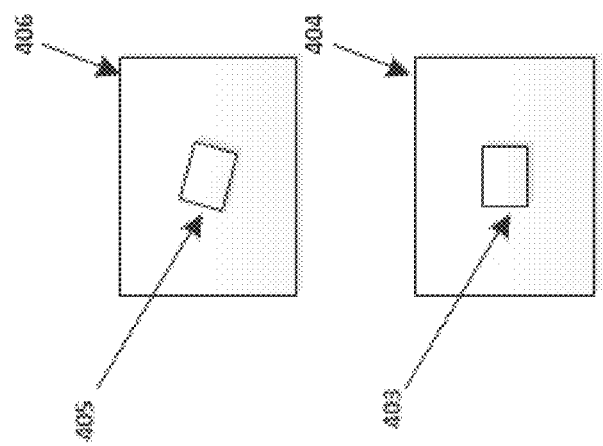

In some instances, the markers may be rotated with respect to one another. For example, shown in FIG. 4A is a first marker 403 placed on a CT gantry 404 and a second marker 405 placed on a PET gantry 406. FIG. 4B shows the perspective from the camera's 401 point-of-view looking down onto the markers, where the second marker 405 on the PET gantry 406 is slightly rotated with respect to the first marker 403 on the CT gantry 404. Because the orientation of each marker can be extracted, even though they are rotated with respect to one another, the image processing circuitry would be able to compensate and properly align the captured images.

Figure 5:
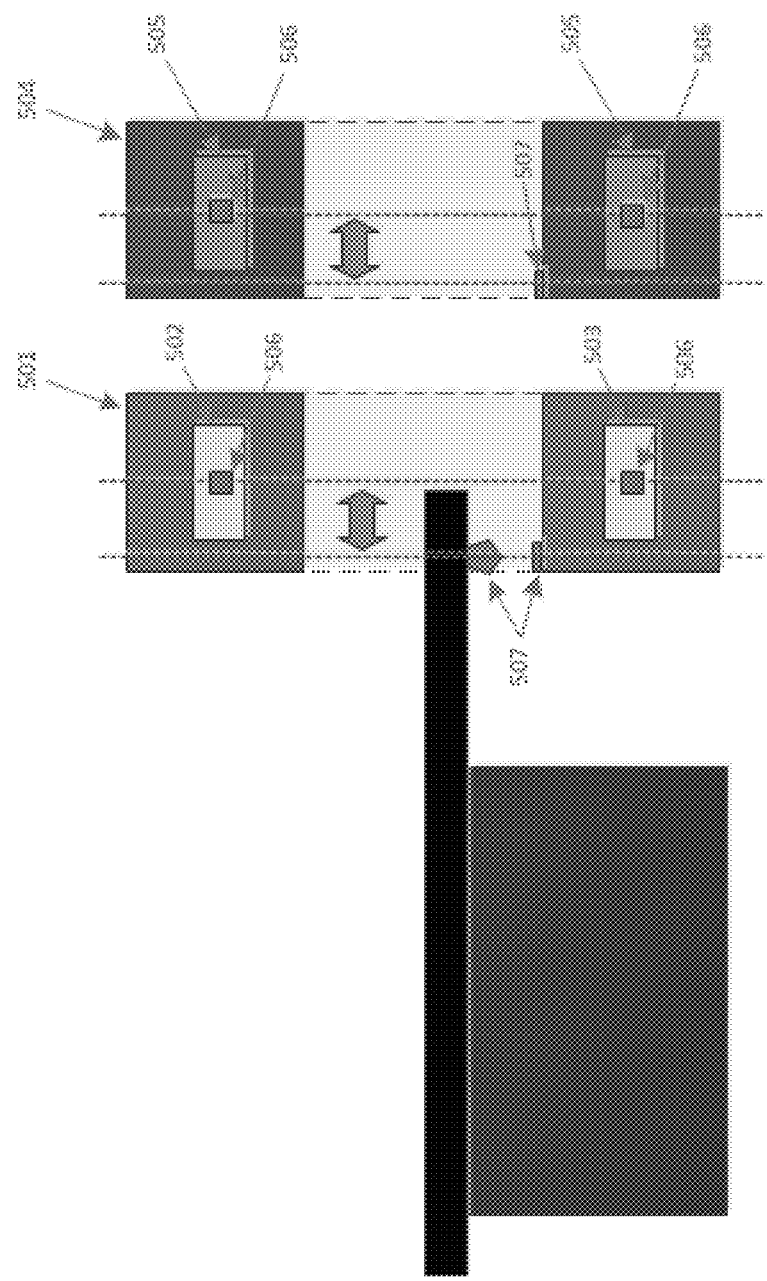
FIG. 5 illustrates a third configuration of a third exemplary embodiment.

Additional tags or cameras can be placed to perform further calibrations on an as needed basis. If any detector elements are disarranged or have defects (e.g. manufactured improperly), they have a way to be identified, calibrated and accounted for. For example, as shown in FIG. 5, a useful calibration could be the alignment of critical detector elements. For the CT gantry 501, the critical alignment elements would be the X-ray tube 502 and CT detector 503. For the PET gantry 504, the critical alignment elements would be the PET detectors 505. Additional optical markers 506 can be placed on these critical elements to determine the location of these critical components relative to each other or any of the other optical devices 507 prior to scanning. If desired, any of the markers can be concealed (e.g. by placing covers over them) and only made visible when needed.

The various described calibrations can be performed each time for every scan, or on a pick-and-choose basis. For example, the gantry-to-gantry calibration can be performed during every routine clinical scan, each time the gantries are moved, each time the covers have been opened/removed, etc. In the description above, the calibration is performed once for each imaging system. In other cases, such as a helical CT scan or continuous bed-motion PET, the calibration can be performed at multiple discrete points in time, and the calibration at any time can then be determined by interpolation. In the case of step-and-shoot PET acquisition, a separate calibration can be determined for each bed position.

Figure 6A:
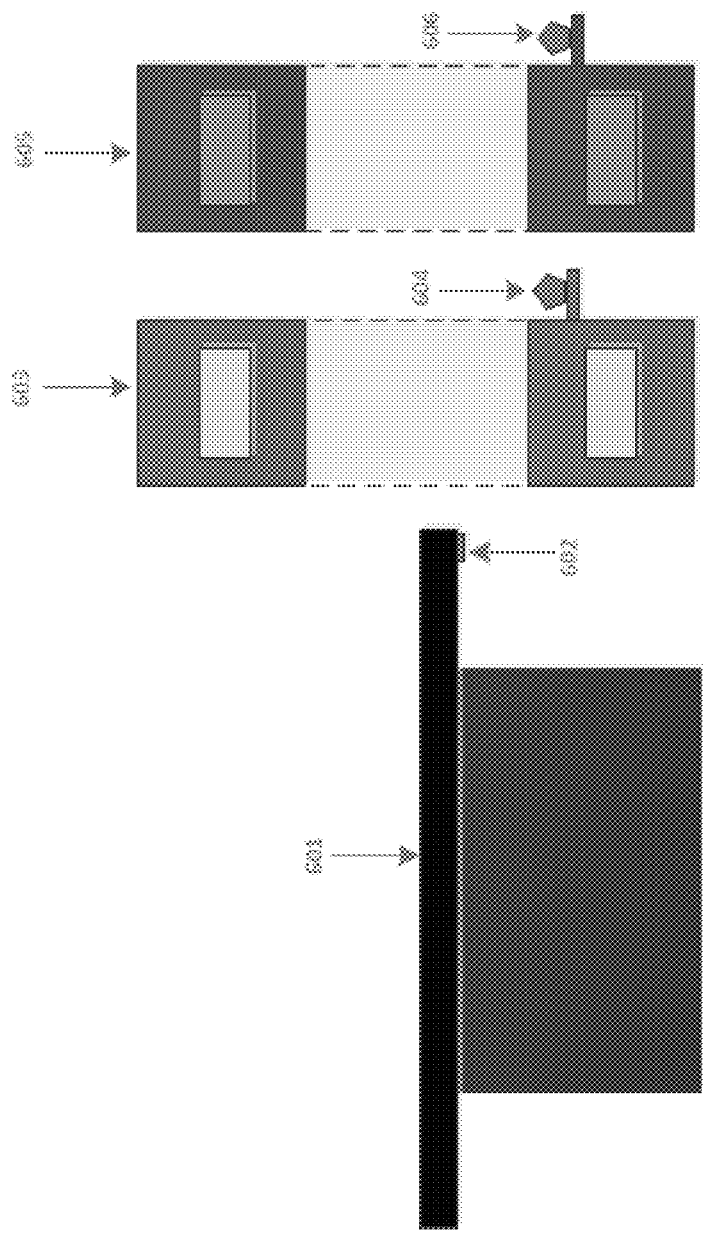
FIGS. 6A-6C illustrate a fourth configuration of a fourth exemplary embodiment of a medical device calibration system as a patient bed progresses from outside first and second medical diagnostic devices to inside the first and second medical devices.
Figure 6B:
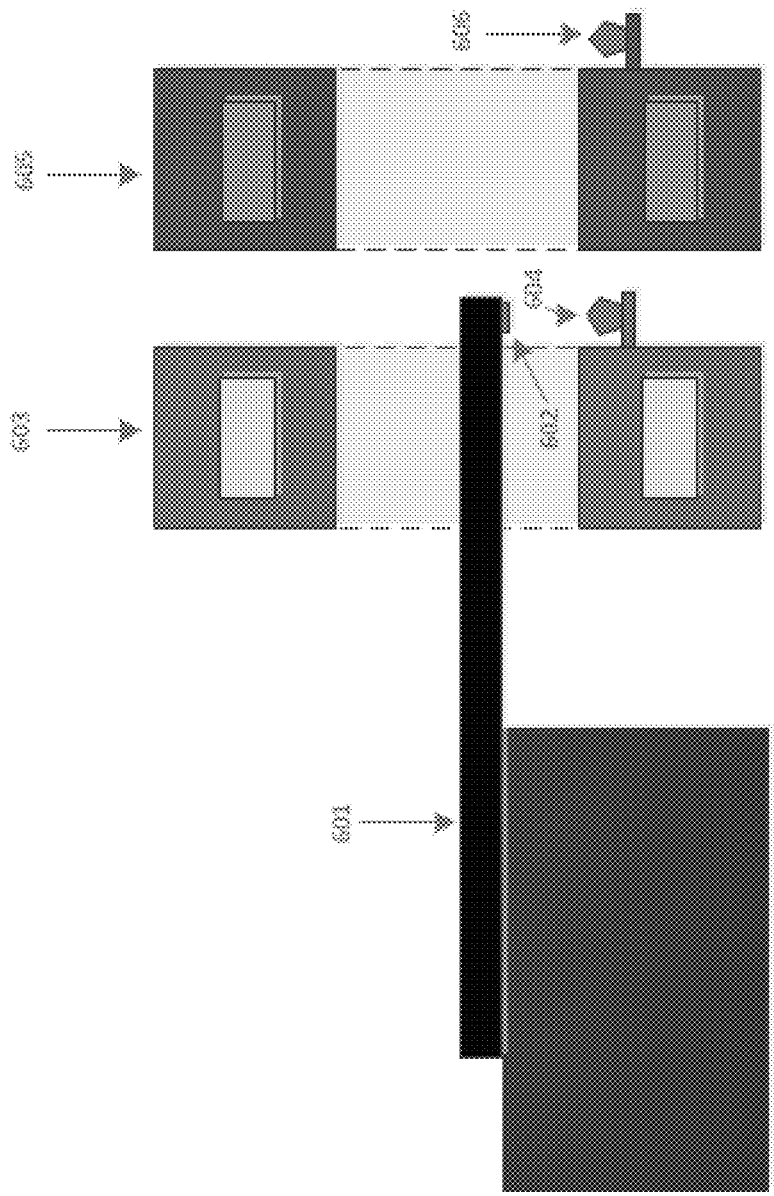
Figure 6C:
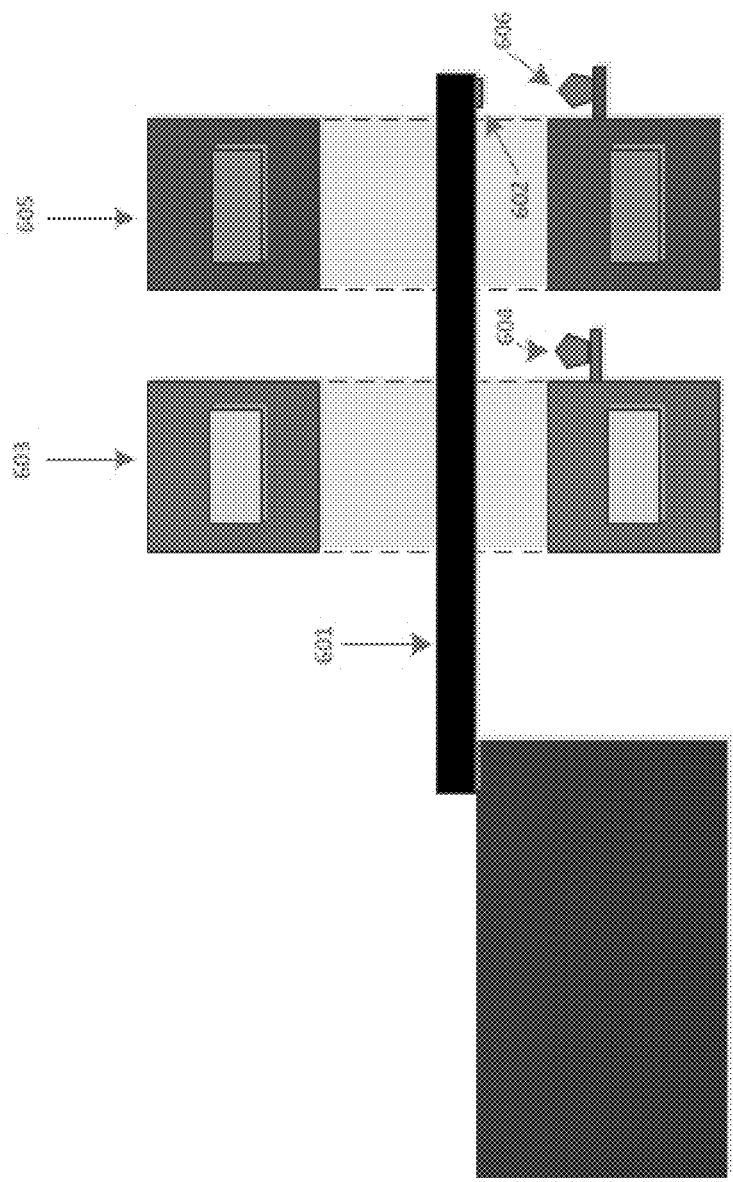

FIGS. 6A-6C help illustrate another embodiment, where one or more optical markers are placed on the patient transportation mechanism, and one or more sensors on placed on the medical imaging devices.

In FIG. 6A, a marker/tag 602 is placed on the patient bed 601, a first camera 604 is placed on the CT gantry 603, and a second camera 606 is placed on the PET gantry 605. The patient bed has not yet entered into either of the gantries The setup may look like this prior to scanning as a default setup, for example. Calibration/coordination can still be taking place though (e.g. gantry-to-gantry calibration, gantry-to-bed calibration). Clinical scanning may or may not be occurring in this configuration. Again, this is because the optical calibration system and the normal function of the scanner are independent operations.

In FIG. 6B, the marker 602 has gone through the CT gantry 603. While the CT scans of the patient are being captured, the first camera 604 captures the position data of the marker 602 for the gantry-to-bed calibration. The captured data from this gantry-to-bed calibration is sent to the processing circuitry.

In FIG. 6C, the marker 602 has gone through the PET gantry 605 and the PET images of the patient are captured. CT images in the first gantry 603 could still be captured during this time too. While the PET scans of the patient are being captured, the camera 606 on the second gantry 605 captures the position data from the marker 602. The captured data from this gantry-to-bed calibration is also sent to the processing circuitry.

Each gantries' gantry-to-bed calibration may occur as its respective gantry is taking images of the patient, but the gantry-to-gantry calibration can be performed any time prior to the images being fused together. After both medical imaging devices have taken the patient's scans, the calibration data is utilized to fuse the PET/CT image.

Figure 7:
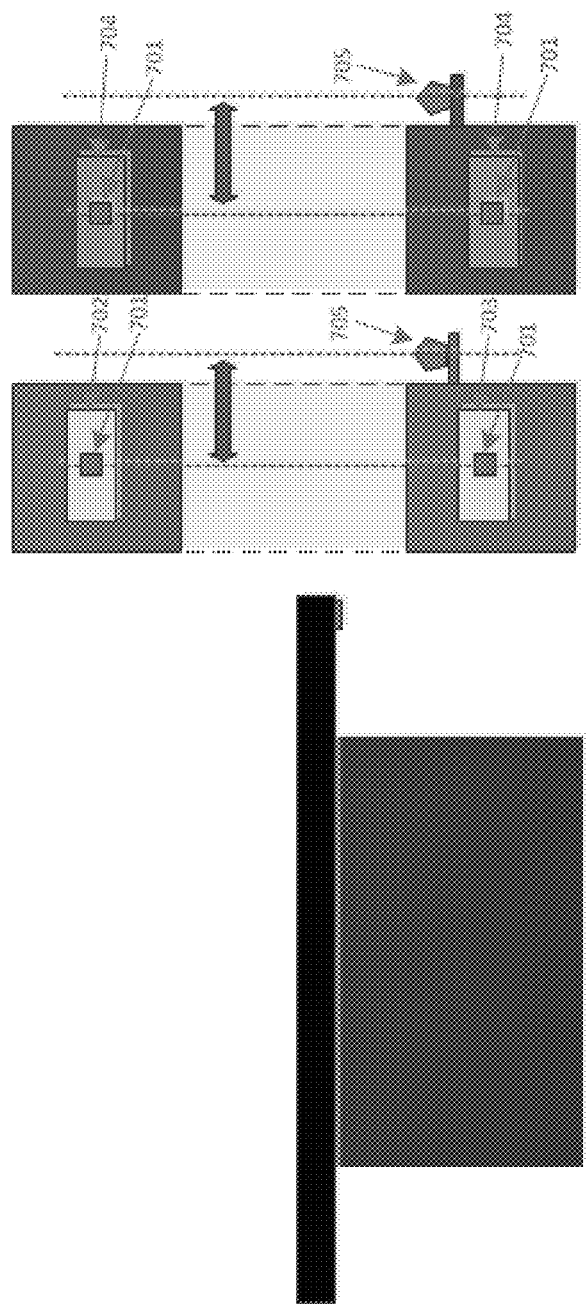
FIG. 7 illustrates a fifth configuration of a fifth exemplary embodiment of a medical device calibration system.

Additional markers or cameras can be placed to perform additional calibrations on an as needed basis. For example, as shown in FIG. 7, markers 701 can be placed on critical components such as the X-ray tube 702, CT detector 703 and PET detectors 704 to determine the location of the cameras 705 relative to these critical components, or the critical components relative to each other.

Figure 8A:
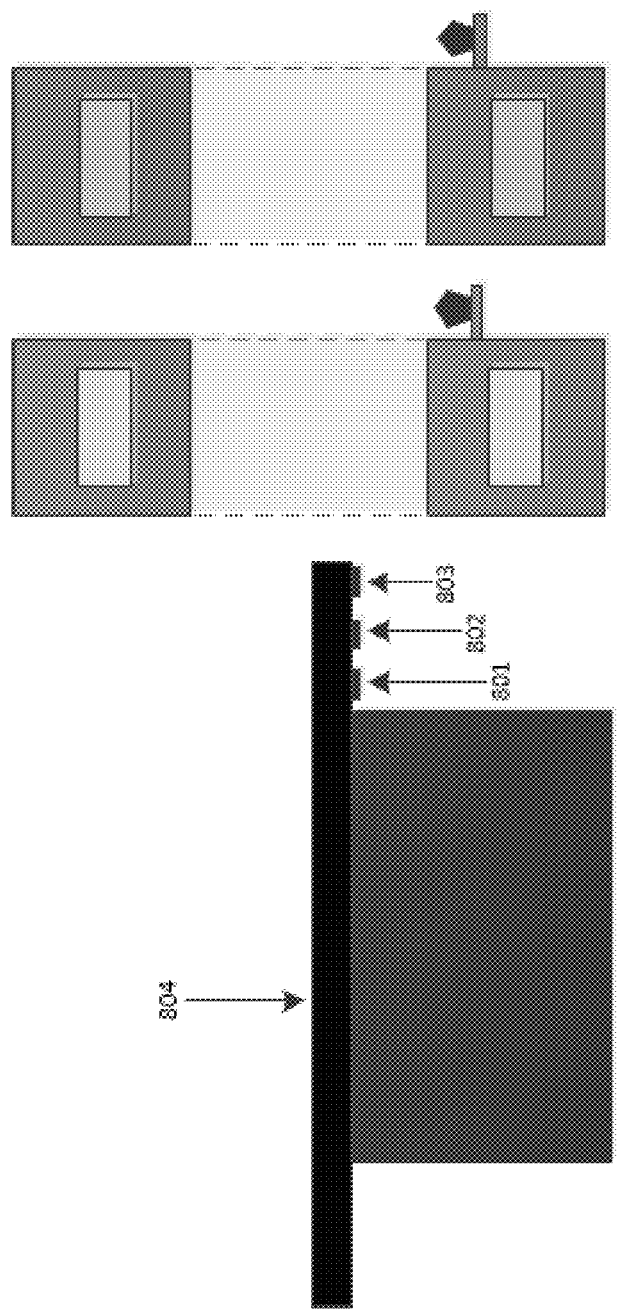
FIGS. 8A and 8B illustrates a sixth configuration of a sixth exemplary embodiment of a medical device calibration system.
Figure 8B:
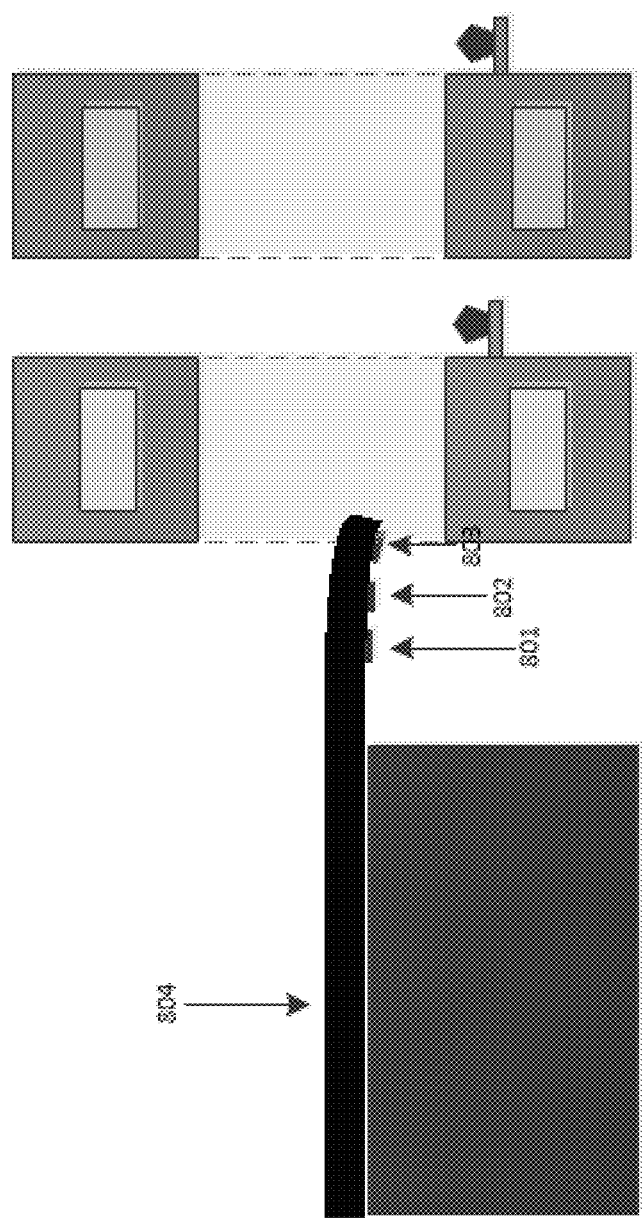

Another embodiment includes image processing that measures deflection of the patient transportation mechanism. Since the use of cameras and optical tags (2-D bar codes), allows for the estimation of 6 degrees of freedom [such as center of tag (x,y,z), direction of normal to the tag (2 angles), and rotation about the normal)], measurements of the movement and orientation changes of a single tag can be used to estimate deflection of a cantilevered bed. One example where these deflections could occur is when a heavy patient is on the patient bed. Continuous bed motion can be assessed with camera-based spatial localization. The continuous bed position (including varying deflection magnitude and direction) information would be integrated with the reconstruction software, where image processing circuitry accounts for deflections (e.g. the patient transportation mechanism moves while performing the scan). For example, during a calibration process prior to scanning patients [e.g. loading the bed with sand-filled bags of different weights (to mimic different body weights) and measuring displacement at different points along the bed as the bed is extended], a model or look-up table can be determined which relates displacement and angle of a tag at the end of the bed to the deflection at various points along the length of the bed. Alternatively, a mechanical finite-element model (FEM) could be used to generate a look-up table to relate measured deflection at one tag position to deflection a various points along the length of the bed. One embodiment for use with a cantilevered bed are shown in FIGS. 8A and 8B. In this case a first tag 801, second tag 802, and third tag 803 are applied along the length of the bed 804, as shown in FIG. 8A. As the bed 804 moves, it has a deflection, as illustrated in FIG. 8B. Even though the bed deflects, at any given time, the position and orientation of each of the tags can be determined by acquiring and processing images from the cameras. The position and orientations of the surface of the bed can then be estimated at other locations by interpolation of the measurements from the tag locations.

Another embodiment includes the use of different optical sensors at various locations for signal averaging (e.g. telephoto lens, wide lens). Each medical imaging device or patient bed could have multiple, different optical sensors affixed to it. Some optical sensor inputs may be weighted more than others in calculating positions and orientations. For example, a camera with a telephoto lens may be weighted more than a wide lens. In another embodiment, a single camera may include a zoom lens which allows acquisition of both wide angle and telephoto views.

Moreover, another embodiment includes using thermal optical sensors (e.g. thermal cameras), thermal optical markers (e.g. infrared emitting tags) and thermal signatures of the apparatus. The optical sensor can detect infrared light and/or ultraviolet light, for instance. The use of thermal sensors may be useful in a case where imaging has to be performed in the dark (as may be the case when performing some types of functional imaging or if the patient is sensitive to light). In this case the tags maybe be made to emit infrared, for example by differential heating of distinct elements in the tag or by use of infrared light-emitting diodes, or the tags may be illuminated by an external infrared light source.

Another embodiment includes the use of multiple optical sensors and/or multiple optical markers for redundancy or additional calibrations. For instance, if a patient or other equipment (e.g. IV holder) blocks one camera or one marker, the system can still function because another camera or marker still has visibility.

Another embodiment includes tags that are machined into the patient transportation mechanism or gantry during the manufacturing process. Machining the tags can be quicker and much more accurate than placing the tags on manually. Furthermore, paint or dye (or similar substance) can be applied to these tags, after machining, to improve visibility. For example, the tags may be in color.

The method and system described herein can be implemented in a number of technologies but generally relate to processing circuitry for performing the processes described herein. In one embodiment, the processing circuitry (e.g., image processing circuitry and controller circuitry) is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include a computer processor and having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores. In an embodiment in which neural networks are used, the processing circuitry used to train the artificial neural network need not be the same as the processing circuitry used to implement the trained artificial neural network that performs the calibration described herein. For example, processor circuitry and memory may be used to produce a trained artificial neural network (e.g., as defined by its interconnections and weights), and an FPGA may be used to implement the trained artificial neural network. Moreover, the training and use of a trained artificial neural network may use a serial implementation or a parallel implementation for increased performance (e.g., by implementing the trained neural network on a parallel processor architecture such as a graphics processor architecture).

In the preceding description, specific details have been set forth, such as a particular method and system for calibrating a patient transportation mechanism using first and second sets of coordinating optical and descriptions of various components and processes used therein. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

The invention claimed is:

1. An apparatus for calibrating a patient transportation mechanism, the apparatus comprising:
    a first set of coordinating optical devices including at least one optical marker;
    a second set of coordinating optical devices including at least one optical sensor for detecting the at least one optical marker;
    and image processing circuitry configured to determine a position of the patient transportation mechanism from a position of the at least one optical marker relative to the at least one optical sensor,
wherein at least one component of one of the first and second sets of coordinating optical devices is configured to be affixed to the patient transportation mechanism, and
wherein at least one component of a remaining one of the first and second sets of coordinating optical devices is configured to be affixed to at least one of first and second medical image diagnostic devices,
wherein one of the first and second medical image diagnostic devices is a PET (Positron Emission computed Tomography) gantry, and wherein a remaining one of the first and second medical image diagnostic devices is a CT (Computed Tomography) gantry or an MRI (Magnetic Resonance Imaging) gantry.

2. The apparatus as claimed in claim 1,
wherein the at least one optical marker comprises a first optical marker configured to be affixed to the patient transportation mechanism, and
wherein the at least one optical sensor comprises (1) a first optical sensor configured to be affixed to the first medical image diagnostic device and (2) a second optical sensor configured to be affixed to the second medical image diagnostic device.

3. The apparatus as claimed in claim 1,
wherein the at least one optical marker comprises (1) a first optical marker configured to be affixed to the first medical image diagnostic device and (2) a second optical medical marker configured to be affixed to the second medical image diagnostic device, and
wherein the at least one optical sensor comprises a first optical sensor configured to be affixed to the patient transportation mechanism.

4. The apparatus as claimed in claim 1,
wherein the at least one optical marker comprises first and second optical markers configured to be affixed to the patient transportation mechanism, and
wherein the at least one optical sensor comprises a first optical sensor configured to be affixed to at least one of the first and second medical image diagnostic devices.

5. The apparatus as claimed in claim 1,
wherein the at least one optical marker comprises a first optical marker configured to be affixed to at least one of the first and second medical image diagnostic devices, and
wherein the at least one optical sensor comprises first and second optical sensors configured to be affixed to the patient transportation mechanism.

6. The apparatus as claimed in claim 1, further comprising controller circuitry configured to:
control movement of the patient transportation mechanism, and
determine the position of the patient transportation mechanism compared to an initial position based on the movement of the patient transportation mechanism.

7. The apparatus of claim 1, further comprising processing circuitry configured to:
determine at least one of a position and an orientation of the at least one optical sensor based on a respective position of each optical marker of the at least one optical marker when the at least one optical marker is affixed to the patient transportation mechanism.

8. The apparatus of claim 1, further comprising processing circuitry configured to:
determine at least one of a position and an orientation of the at least one optical sensor based on a respective relative position of each optical marker of the at least one optical marker when the at least one optical marker is affixed to the patient transportation mechanism.

9. The apparatus as claimed in claim 1, wherein the at least one optical marker comprises one or more optical markers configured to be affixed to the patient transportation mechanism along a direction of motion of the patient transportation mechanism between the first and second medical image diagnostic devices,
wherein the apparatus further comprises at least one optical sensor adjacent to the patient transportation mechanism, and
wherein the image processing circuitry further comprises image processing circuitry for measuring at least one of a deflection magnitude and a deflection direction of the one or more optical markers as the patient transportation mechanism moves in the direction of motion.

10. The apparatus as claimed in claim 1, wherein the at least one optical sensor comprises a camera detecting visible light.

11. The apparatus as claimed in claim 1, wherein the at least one optical sensor comprises a camera detecting at least one of infrared light and ultraviolet light.

12. The apparatus as claimed in claim 1, wherein the at least one optical marker comprises a two-dimensional barcode.

13. The apparatus as claimed in claim 1, wherein the at least one optical marker comprises an infrared emitting tag.

14. The apparatus as claimed in claim 1, wherein the at least one optical marker is machined into the patient transportation mechanism.

15. The apparatus as claimed in claim 14, wherein the at least one machined optical marker comprises a painted machined optical marker painted after machining.

16. The apparatus as claimed in claim 1, wherein the at least one optical marker is machined into the patient transportation mechanism at a time of manufacture of the patient transportation mechanism.

17. A method for calibrating patient transportation mechanism, the method comprising:
providing a first set of coordinating optical deg ices including at least one optical marker;
providing a second set of coordinating optical deg ices including at least one optical sensor;
detecting an image of the at least one optical marker using the at least one optical sensor; and
determining a position of the patient transportation mechanism from a position of the at least one optical marker relative to the at least one optical sensor,
wherein at least one component of one of the first and second sets of coordinating optical devices is configured to be affixed to the patient transportation mechanism, and
wherein at least one component of a remaining one of the first and second sets of coordinating optical devices is configured to be affixed to at least one of first and second medical image diagnostic devices,
wherein one of the first and second medical image diagnostic devices is a PET (Positron Emission computed Tomography) gantry, and wherein a remaining one of the first and second medical image diagnostic devices is a CT (Computed Tomography) gantry or an MRI (Magnetic Resonance Imaging) gantry.

18. A non-transitory computer readable medium having computer instructions stored therein for, when interacting with a first set of coordinating optical devices including at least one optical marker, and when interacting with a second set of coordinating optical devices including at least one optical sensor; causing processing circuitry under control of the computer instructions to perform the steps of detecting an image of the at least one optical marker using the at least one optical sensor, and determining a position of the patient transportation mechanism from a position of the at least one optical marker relative to the at least one optical sensor, wherein at least one component of one of the first and second sets of coordinating optical devices is configured to be affixed to the patient transportation mechanism, and wherein at least one component of a remaining one of the first and second sets of coordinating optical devices is configured to be affixed to at least one of first and second medical image diagnostic devices, wherein one of the first and second medical image diagnostic devices is a PET (Positron Emission computed Tomography) gantry, and wherein a remaining one of the first and second medical image diagnostic devices is a CT (Computed Tomography) gantry or an MRI (Magnetic Resonance Imaging) gantry.

19. An apparatus for calibrating a patient transportation mechanism, the apparatus comprising:

a first set of coordinating optical devices including at least one optical marker;

a second set of coordinating optical devices including at least one optical sensor for detecting the at least one optical marker, and image processing circuitry configured to determine a position of the patient transportation mechanism from a position of the at least one optical marker relative to the at least one optical sensor, wherein at least one component of one of the first and second sets of coordinating optical devices is configured to be affixed to the patient transportation mechanism, wherein at least one component of a remaining one of the first and second sets of coordinating optical devices is configured to be affixed to at least one of first and second medical image diagnostic devices, wherein the at least one optical marker comprises a first optical marker configured to be affixed to the patient transportation mechanism, and wherein the at least one optical sensor comprises (1) a first optical sensor configured to be affixed to the first medical image diagnostic device and (2) a second optical sensor configured to be affixed to the second medical image diagnostic device.

20. An apparatus for calibrating a patient transportation mechanism, the apparatus comprising:

a first set of coordinating optical devices including at least one optical marker;

a second set of coordinating optical devices including at least one optical sensor for detecting the at least one optical marker, and image processing circuitry configured to determine a position of the patient transportation mechanism from a position of the at least one optical marker relative to the at least one optical sensor, wherein at least one component of one of the first and second sets of coordinating optical devices is configured to be affixed to the patient transportation mechanism, wherein at least one component of a remaining one of the first and second sets of coordinating optical devices is configured to be affixed to at least one of first and second medical image diagnostic devices, wherein the at least one optical marker comprises (1) a first optical marker configured to be affixed to the first medical image diagnostic device and (2) a second optical medical marker configured to be affixed to the second medical image diagnostic device, and wherein the at least one optical sensor comprises a first optical sensor configured to be affixed to the patient transportation mechanism.

21. An apparatus for calibrating a patient transportation mechanism, the apparatus comprising:

a first set of coordinating optical devices including at least one optical marker;

a second set of coordinating optical devices including at least one optical sensor for detecting the at least one optical marker, and image processing circuitry configured to determine a position of the patient transportation mechanism from a position of the at least one optical marker relative to the at least one optical sensor, wherein at least one component of one of the first and second sets of coordinating optical devices is configured to be affixed to the patient transportation mechanism, wherein at least one component of a remaining one of the first and second sets of coordinating optical devices is configured to be affixed to at least one of first and second medical image diagnostic devices, wherein the at least one optical marker comprises one or more optical markers configured to be affixed to the patient transportation mechanism along a direction of motion of the patient transportation mechanism between the first and second medical image diagnostic devices, wherein the apparatus further comprises at least one optical sensor adjacent to the patient transportation mechanism, and wherein the image processing circuitry further comprises image processing circuitry for measuring at least one of a deflection magnitude and a deflection direction of the one or more optical markers as the patient transportation mechanism moves in the direction of motion.

22. An apparatus for calibrating a patient transportation mechanism, the apparatus comprising:

a first set of coordinating optical devices including at least one optical marker;

a second set of coordinating optical devices including at least one optical sensor for detecting the at least one optical marker, and image processing circuitry configured to determine a position of the patient transportation mechanism from a position of the at least one optical marker relative to the at least one optical sensor, wherein at least one component of one of the first and second sets of coordinating optical devices is configured to be affixed to the patient transportation mechanism, wherein at least one component of a remaining one of the first and second sets of coordinating optical devices is configured to be affixed to at least one of first and second medical image diagnostic devices, wherein the at least one optical marker is machined into the patient transportation mechanism, and wherein the at least one machined optical marker comprises a painted machined optical marker painted after machining.

\* \* \* \* \*